(12) United States Patent
Barroso Villa

(10) Patent No.: US 11,399,869 B2
(45) Date of Patent: Aug. 2, 2022

(54) CANNULA STABILIZER FOR EMBRYO TRANSFER

(71) Applicant: Juan Gerardo Barroso Villa, Cuajimalpa de Morelos (MX)

(72) Inventor: Juan Gerardo Barroso Villa, Cuajimalpa de Morelos (MX)

( * ) Notice: Subject to any disclaimer, the term of this patent is extended or adjusted under 35 U.S.C. 154(b) by 171 days.

(21) Appl. No.: 16/995,331

(22) Filed: Aug. 17, 2020

(65) Prior Publication Data
US 2021/0393293 A1 Dec. 23, 2021

(30) Foreign Application Priority Data
Jun. 18, 2020 (MX) .................. MX/A/2020/006458

(51) Int. Cl.
| | | |
|---|---|---|
| *A61B 1/32* | (2006.01) | |
| *A61B 17/34* | (2006.01) | |
| *A61B 17/435* | (2006.01) | |
| *A61B 90/00* | (2016.01) | |
| *A61B 17/00* | (2006.01) | |

(52) U.S. Cl.
CPC ............ *A61B 17/3496* (2013.01); *A61B 1/32* (2013.01); *A61B 17/3421* (2013.01); *A61B 17/435* (2013.01); *A61B 90/06* (2016.02); *A61B 2017/00902* (2013.01); *A61B 2017/345* (2013.01)

(58) Field of Classification Search
CPC combination set(s) only.
See application file for complete search history.

(56) References Cited

U.S. PATENT DOCUMENTS

| | | | |
|---|---|---|---|
| 3,037,505 A | | 6/1962 | Walden et al. |
| 3,320,948 A | | 5/1967 | Martin |
| 3,789,829 A | | 2/1974 | Hasson |
| 4,323,057 A | | 4/1982 | Jamieson |
| 5,026,368 A | | 6/1991 | Adair |
| 5,167,222 A | | 12/1992 | Schinkel et al. |
| 5,458,595 A | | 10/1995 | Tadir et al. |
| 5,700,268 A | * | 12/1997 | Bertin .................... A61B 90/06 606/102 |
| 2005/0085699 A1 | | 4/2005 | Weiss |
| 2008/0306345 A1 | | 12/2008 | Balas |
| 2011/0245618 A1 | | 10/2011 | Fenster et al. |
| 2017/0333017 A1 | | 11/2017 | Gifford et al. |

FOREIGN PATENT DOCUMENTS

| | | |
|---|---|---|
| CA | 2996350 A1 | 3/2017 |
| FR | 820618 A | 11/1937 |
| GB | 330629 A | 6/1930 |
| GB | 2391815 B | 9/2005 |
| WO | 2011051517 A1 | 5/2011 |
| WO | 2012010857 A1 | 1/2012 |
| WO | 2018185742 A1 | 10/2018 |

* cited by examiner

*Primary Examiner* — Sameh R Boles
(74) *Attorney, Agent, or Firm* — Ryan T. Grace; Advent, LLP

(57) ABSTRACT

The embryo transfer cannula stabilizer is a device attached to a vaginal speculum, which allows the sliding, placement, and secure fixing of a cannula to perform an embryo transfer. The embryo transfer cannula stabilizer prevents fine movement of the user's hand to reduce tremor at the intracervical level and avoid injury to the cervical canal, rupture of blood vessels, and the production of detritus.

5 Claims, 3 Drawing Sheets

CANNULA STABILIZER FOR EMBRYO TRANSFER

SUBJECT MATTER OF THE INVENTION

The embryo transfer cannula stabilizer is a device attached to a vaginal speculum, which allows the sliding, placement, and secure fixing of a cannula to perform an embryo transfer. The embryo transfer cannula stabilizer prevents fine movement of the user's hand to reduce tremor at the intracervical level and avoid injury to the cervical canal, rupture of blood vessels, and the production of detritus.

BACKGROUND

During the embryo transfer process, a variety of complicated static manual maneuvers must be performed for periods of time that require precision. These maneuvers compromise mobility due to obstruction of a hand and the movements of it into one position, leaving said hand fixed. This results in numbness, tiredness and when the position is withdrawn in staggered movements, which results in the technique not being reproducible.

Additionally, due to the lack of stability for the cervix insertion catheter from its introduction into the vaginal speculum, the surgeon's hand is obstructed as mentioned above.

To solve these problems, the device of the present invention has been designed so as to effectively solve the following problems:

a) Providing stability to the catheter;
b) Avoiding using the surgeon's hands once the catheter is stabilized;
c) Keeping the surgeon's hands free so that they can interact with each other in other parts of the procedure that are required, using their own ergonomics in the technique to be performed, in addition to helping the surgeon's posture in general; and
d) To avoid the presence of bleeding into the catheter (with impairment in embryo implantation) during cannula insertion due to vessel breakdown for hand tremor.

BRIEF DESCRIPTION OF THE INVENTION

The present invention relates to an embryo transfer cannula stabilizer comprising a main body with a distal end and a proximal end; the main body having a longitudinal groove; the distal end having at least one cavity; and the proximal end having a support element.

BRIEF DESCRIPTION OF THE FIGURES

The illustrative modality can be described with reference to the accompanying figures, which relate to.

DETAILED DESCRIPTION OF THE INVENTION

The following detailed description is exemplary only and is not intended to limit the disclosed modalities or the application and uses of the described modalities. As used herein, the word "exemplary" or "illustrative" means "serving as an example, instance, or illustration". Any implementation described herein as "exemplary" or "illustrative" should not necessarily be construed as preferred or advantageous over other implementations. All of the implementations described below are exemplary implementations provided to enable those skilled in the art to make or use the modalities of the disclosure and are not intended to limit the scope of the disclosure. For the purposes of the present description, the terms "upper", "lower", "left", "posterior", "right", "front", "vertical", "horizontal" and their derivatives will refer to the invention as oriented in the figures. Furthermore, there is no intention to be subject to any explicit or implicit theory presented in the technical field above, background, brief summary or the following detailed description. It should also be understood that the specific devices and processes illustrated in the accompanying drawings, and described in the following specification, are simply exemplary modalities of the inventive concepts defined in the attached claims. Therefore, the specific dimensions and other physical characteristics related to the modalities described herein should not be considered as limiting, unless the claims expressly state otherwise.

Figure 1:
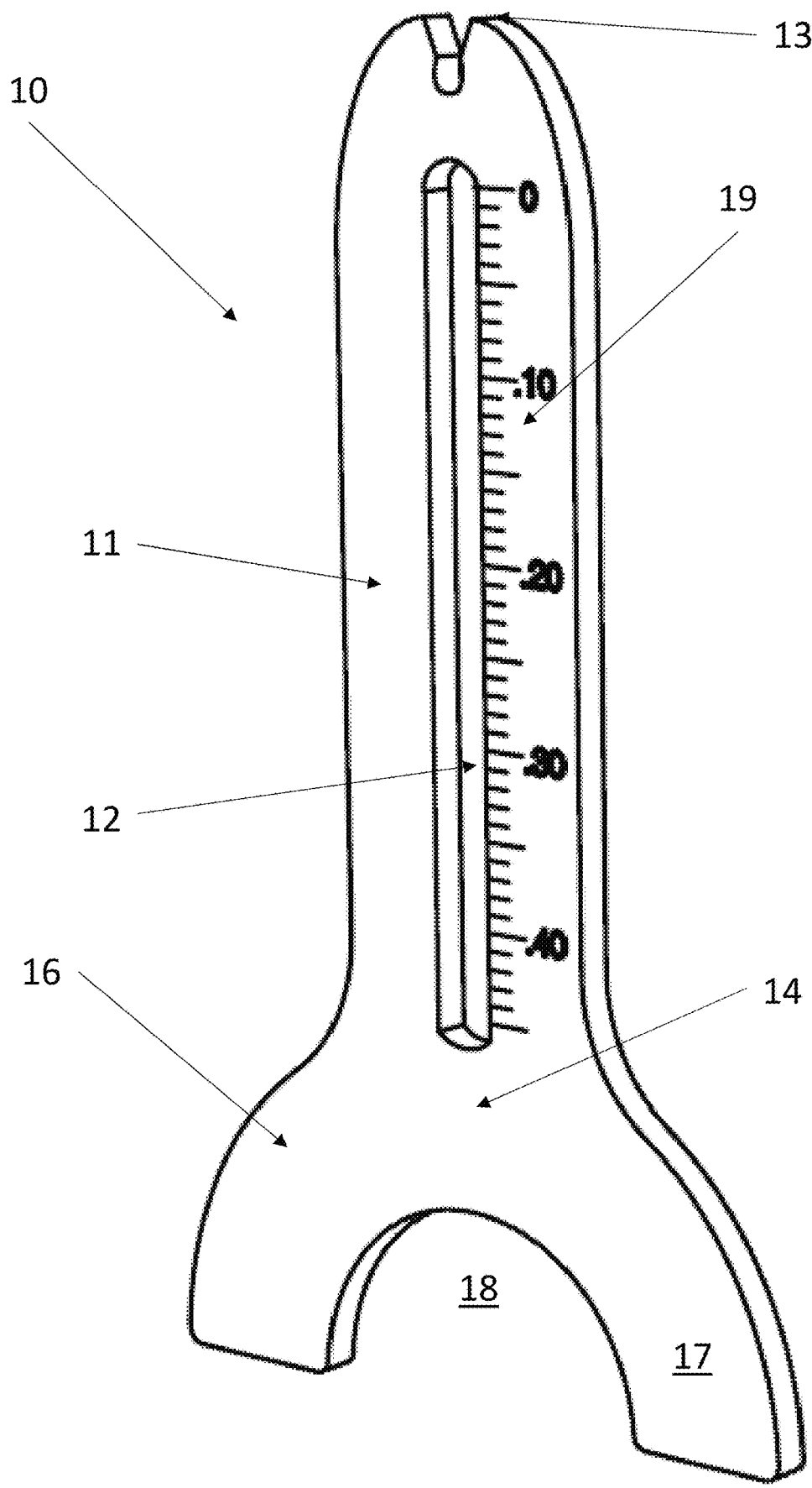
FIG. 1 is a front view of the embryo transfer cannula stabilizer of the present invention.

FIG. 1 shows the embryo transfer cannula stabilizer (10) comprising a main body (11), preferably elongated, the main body having a longitudinal groove (12), said longitudinal groove (12) being aligned with a longitudinal axis of the main body (11); and a measurement scale (19) being located to one side of the longitudinal groove (12).

Figure 2:
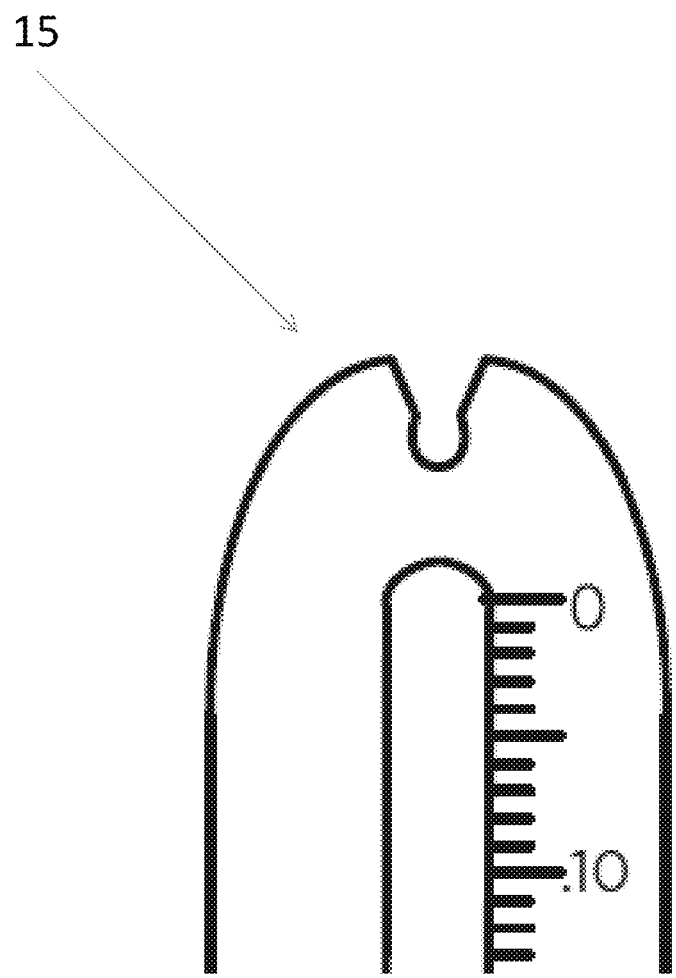
FIG. 2 is a detail view of the distal end of the embryo transfer cannula stabilizer of the present invention.

Said main body (11) has a distal end (13) and a proximal end (14), diametrically opposed to each other; in FIG. 2 it is observed that said distal end (13) has at least one cavity (15), said cavity (15) being aligned with said longitudinal axis, additionally, the number of preferred cavities (15) being three cavities, said three cavities having three diameters different from each other, so that the cavity with a larger diameter is located in the outermost part of the distal end (13), while the cavity with a smaller diameter is located in the innermost part of the distal end.

The proximal end (14) has a support element (16), said support element (16) comprising a pair of arms (17) that extend longitudinally towards said proximal end (14) and an arc (18) arranged between the arms (17).

The embryo transfer cannula stabilizer (10) is made of a transparent material, the transparent material being chosen from the group of crystal polystyrene, solid polycarbonate, polypropylene, acrylic, PET, PVC, glass, crystal, cane bagasse, wheat bagasse, agave fiber, and PLA, among others.

Figure 3:
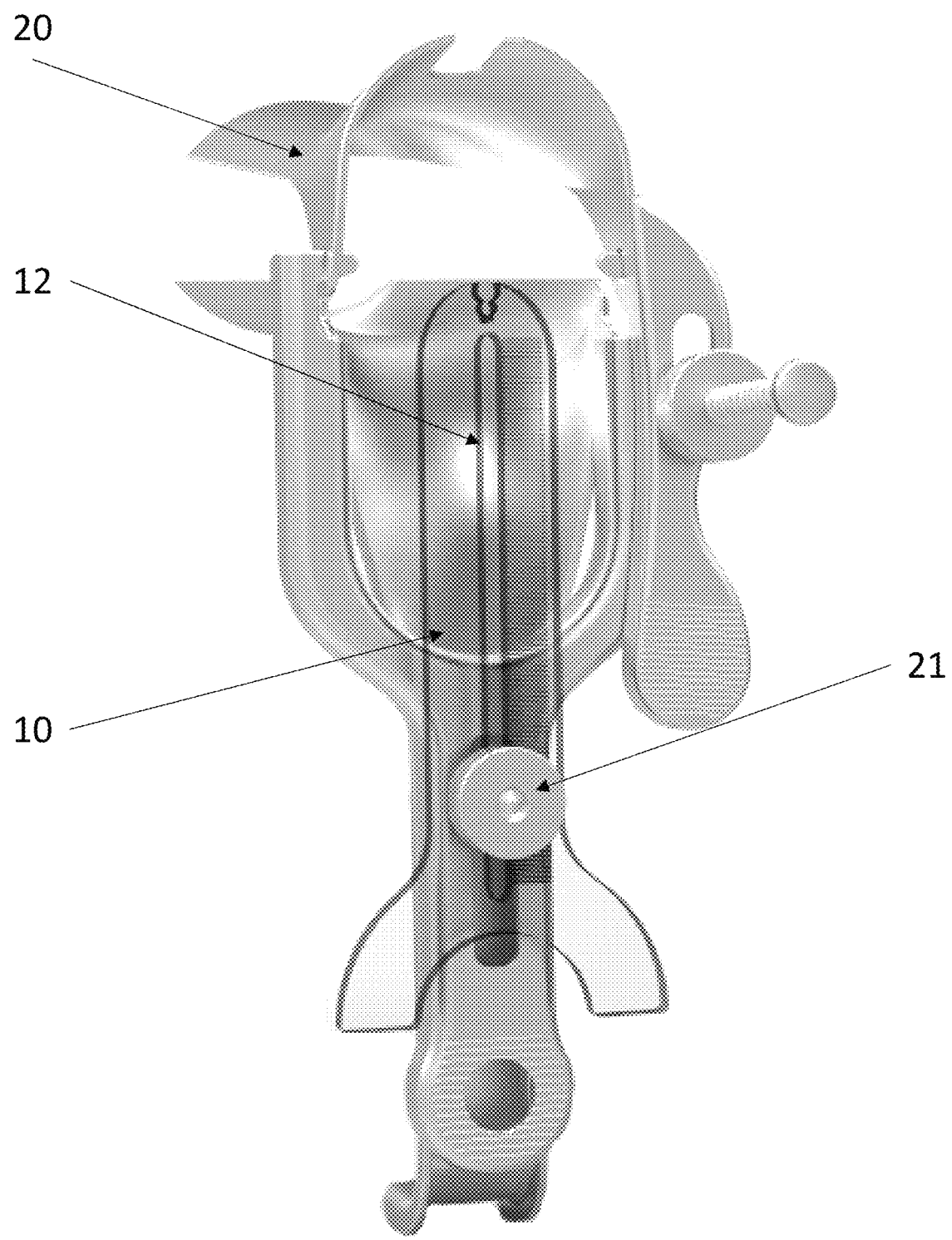
FIG. 3 is a perspective view of the embryo transfer cannula stabilizer of the present invention coupled with a vaginal speculum.

It can be seen in FIG. 3 that the embryo transfer cannula stabilizer (10) is configured to be coupled with a vaginal speculum (20) by a coupling means (21), preferably a screw, which passes through the longitudinal groove (12) and is fastened to said vaginal speculum (20).

The method of use of the embryo transfer cannula stabilizer (10) is as follows:

1. Prior to initiating an embryo transfer procedure, the longitudinal groove of the embryo transfer cannula stabilizer should be placed over the Y-shaped handle of the vaginal speculum (20) to be secured with the mirror handle nut.

2. The patient is placed in a lithotomy position and asepsis and antisepsis are performed. The user takes the vaginal speculum (20) at 45° with the right hand and inserts it diagonally over the patient's vaginal canal.

3. By opening the upper and lower leaves of the vaginal speculum (20), the user visualizes the presence of the cervical opening and fixes the desired position with the lever nut of the speculum (20) for the cervical examination of the patient.

4. The support element ( ) of the embryo transfer cannula stabilizer (10) allows the user to carry out a rotation of up to 90° on both sides (right and left) with the index finger to allow vaginal cleaning through of the upper and lower leaves of the vaginal speculum (20).

5. The longitudinal slot ( ) of the embryo transfer cannula stabilizer (10) allows the user to adjust the height of the stabilizer based on the gradual scale ( ), using the handle nut of the vaginal speculum (20) to set the desired level.

6. Finally, the embryo transfer cannula is placed and slides over the at least one cavity ( ) of the embryo transfer cannula stabilizer (10) which, once the desired position is located, can be fixed to prevent movement of the hand while performing the embryo transfer.

The present invention is suitable for various modifications and alternative constructions, some of which are detailed in the drawings below. However, it should be clear that the intention is not to limit the invention to a particular modality or form, but rather the present invention should cover changes, additions and modifications as part of its scope. Independent aspects and advantages of the present invention will become apparent to those skilled in the art upon review of the detailed description and drawings.

A person skilled in the art can modify the structure described herein. However, it should be noted that this description relates to preferred modalities of the invention, and is provided for illustrative purposes only, and should not be understood as limiting the invention. All obvious modifications in the spirit of the invention, such as changes in the shape, material, and dimensions of the elements that make up the invention, should be considered within the scope of the attached claims.

The invention claimed is:

1. A cannula stabilizer for embryo transfer comprising: a main body with a distal end and a proximal end, wherein the distal end of the main body has three cavities, wherein said three cavities are longitudinally aligned, wherein said three cavities have three diameters different from each other, so that the cavity with a larger diameter is located in the outermost part of the distal end, while the cavity with a smaller diameter is located in the innermost part of the distal end; the main body having a longitudinal groove, wherein the longitudinal groove is aligned with a longitudinal axis of the main body, wherein a measurement scale is located on one side of the longitudinal groove; and the proximal end having a support element, wherein the support element comprises a pair of arms extending longitudinally towards said proximal end and an arc arranged between the arms.

2. The embryo transfer cannula stabilizer according to claim 1, wherein said stabilizer is made of a transparent material.

3. The embryo transfer cannula stabilizer according to claim 2, wherein the transparent material is chosen from at least one member of a group comprising: crystal polystyrene, solid polycarbonate, polypropylene, acrylic, PET, PVC, glass, crystal, cane bagasse, wheat bagasse, agave fiber, and PLA.

4. The embryo transfer cannula stabilizer according to claim 1, wherein the stabilizer is configured to be coupled with a vaginal speculum by a coupling means passing through the longitudinal groove and fastened to said vaginal speculum.

5. The embryo transfer cannula stabilizer according to claim 4, wherein said coupling means comprises a screw.

\* \* \* \* \*